(12) United States Patent
Gliessmann

(10) Patent No.: US 8,907,308 B2
(45) Date of Patent: Dec. 9, 2014

(54) METHOD AND APPARATUS FOR VERIFYING AN IRRADIATION FIELD

(75) Inventor: Stefan Gliessmann, Campbell, CA (US)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/605,897

(22) Filed: Sep. 6, 2012

(65) Prior Publication Data

US 2013/0243157 A1 Sep. 19, 2013

(30) Foreign Application Priority Data

Sep. 7, 2011 (DE) .......................... 10 2011 082 257

(51) Int. Cl.
*G21K 5/04* (2006.01)
*A61N 5/10* (2006.01)

(52) U.S. Cl.
CPC ............ *A61N 5/1049* (2013.01); *A61N 5/1045* (2013.01); *A61N 5/1067* (2013.01); *A61N 2005/105* (2013.01)
USPC .................. 250/492.3; 250/491.1; 250/492.1; 250/396 R; 250/397

(58) Field of Classification Search
USPC ............ 250/491.1, 492.1, 492.3, 396 R, 397
See application file for complete search history.

(56) References Cited

U.S. PATENT DOCUMENTS

| 7,697,147 | B2 | 4/2010 | Kindlein | |
| 2008/0049896 | A1* | 2/2008 | Kuduvalli | ...................... 378/65 |
| 2009/0292200 | A1 | 11/2009 | Kindlein et al. | |
| 2011/0233423 | A1* | 9/2011 | Balakin | ................... 250/454.11 |

FOREIGN PATENT DOCUMENTS

DE 10 2008 012 496 A1 9/2009
DE 10 2008 025 014 A1 11/2009

OTHER PUBLICATIONS

German Office Action dated Aug. 8, 2012 for corresponding German Patent Application No. DE 10 2011 082 257.7 with English translation.

* cited by examiner

*Primary Examiner* — Nicole Ippolito
(74) *Attorney, Agent, or Firm* — Lempia Summerfield Katz LLC

(57) ABSTRACT

A radiation therapy device includes an irradiation field limiting apparatus. The irradiation field limiting apparatus includes a collimator for adjusting the irradiation field, and a verification apparatus for visually verifying the irradiation field. The verification apparatus is configured such that the irradiation field is optically displayed on a patient that is positioned at a distance from the isocenter of the radiation therapy device.

19 Claims, 1 Drawing Sheet

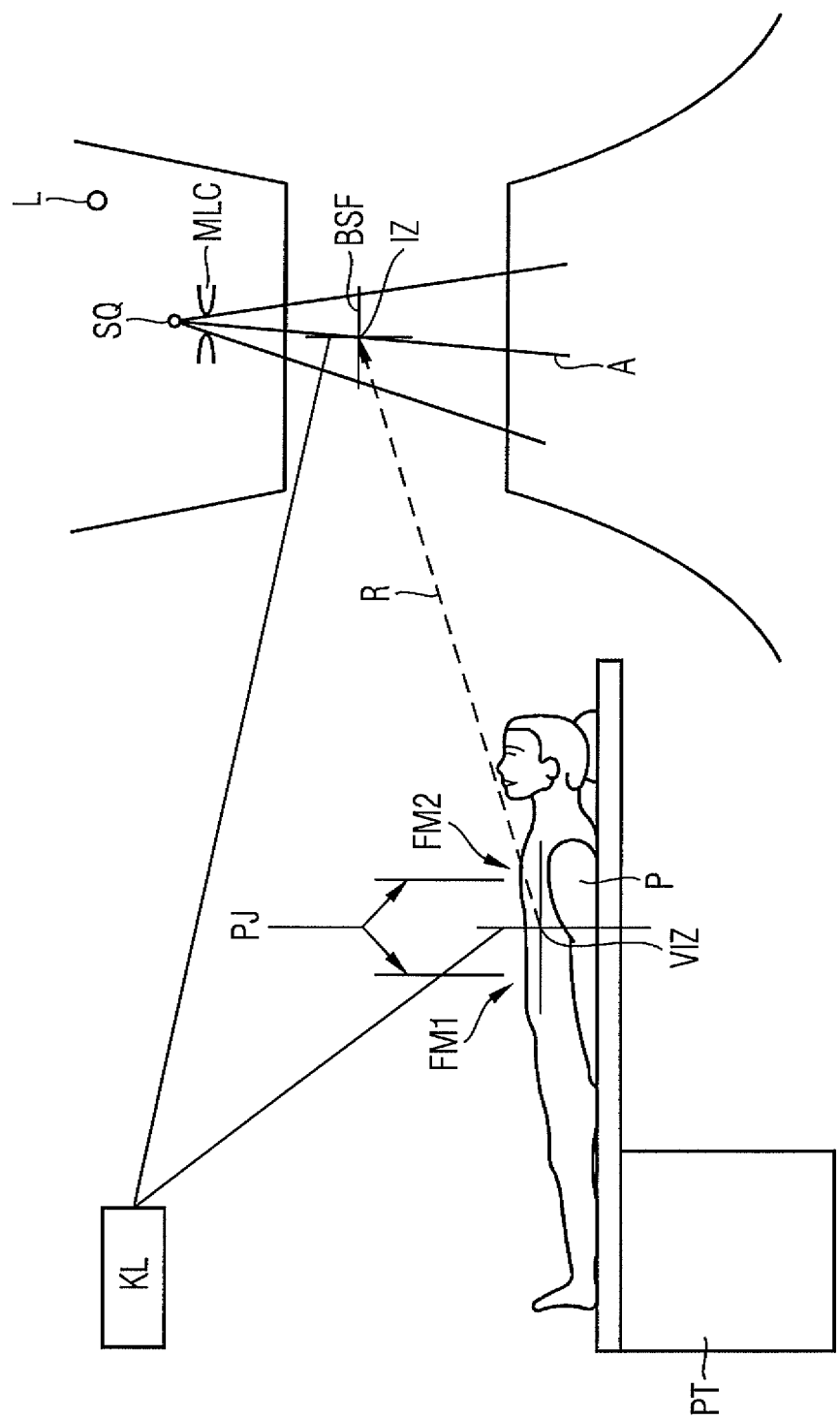

METHOD AND APPARATUS FOR VERIFYING AN IRRADIATION FIELD

This application claims the benefit of DE 10 2011 082 257.7, filed on Sep. 7, 2011.

BACKGROUND

The present embodiments relate to a method and an apparatus for verifying an irradiation field.

Radiation therapy is an established method, in which ionizing radiation is used to treat pathological tissue (e.g., tumor tissue). The aim of radiation therapy is to irradiate the tissue to be treated with an adequate therapeutic dose and in the process, simultaneously protect the healthy surrounding tissue. The therapeutic effect is based, for example, on tumor cells generally having a poorer ability to repair for DNA damage on account of ionizing radiation than cells of healthy tissue.

Image guided radiation therapy (IGRT) enables uncertainties in the irradiation of the target volume to be reduced. IGRT allows visualization of the target volume, organs at risk (OAR) and healthy surrounding tissue prior to the start of an irradiation in order to open up the possibility of irradiating the target volume more precisely.

In order to be able to better determine patient changes between the fractions, a computed tomography recording (also CT for computed tomography) may be produced on the same couch prior to each irradiation. The position of the tumor may therefore be readjusted.

In order to observe the patient movement during the irradiation, the MV therapy beam may also be used for projection imaging (e.g., "portal imaging"). Systems also exist that, in addition to the MV therapy beam, also have a further x-ray source and an additional x-ray sensitive detector. Aside from projective monitoring of the patient movement, CT imaging may therefore also be operated as a movement control.

Sectional views are used to create irradiation plans for radiation therapy. The sectional views represent the region to be irradiated in a three-dimensional manner. CT images are predominantly used.

A light source may be used in radio oncology for a visual check of an irradiation field. The light source is collimated by the multi level collimator (MLC). The field thus projected is made congruent or in alignment with patient markers using patient couch movements. If congruence is achieved, the irradiation field is verified visually.

In the emitter head of the medical linear accelerator (LINAC), a light source is projected into the radiation path via a mirror. The adjustment of the light source and also of the mirror is very time-consuming and is regularly controlled by the user. A useful installation height along the radiation axis is provided on account of the mirror that may be moved to and fro into the radiation path.

SUMMARY AND DESCRIPTION

The present embodiments may obviate one or more of the drawbacks or limitations in the related art. For example, a method that results in an accurate and precise beam application is provided.

In one embodiment, a virtual isocenter in an imaging system is combined with a projection of an irradiation field (e.g., similar to a virtual simulation) in order to achieve an optimization in a process flow in radio oncology.

In this process, the patient and/or tumor may assume a position at a distance from the isocenter and/or a position outside of the isocenter in order to visually control the irradiation field. After controlling the irradiation field, the patient and/or the tumor to be irradiated is repositioned for irradiation in the isocenter. This repositioning includes a larger movement and may not be equated with repositionings in which the patient is already positioned in the isocenter and in which only a small position correction is performed for the irradiation in order to compensate for possible position inaccuracies in the tumor. An off-isocentric position of the patient lying outside of the isocenter may include a distance, for example, of more than 20 cm, 30 cm or even 450 cm from the isocenter.

The patient may be adjusted to a height (e.g., virtual isocenter) that is optimal for clinical personnel and brings about ergonomic advantages. The clinical personnel are to verify the congruence of the projection with the patient markers and/or field markers from different directions. A virtual isocenter that is arranged low is advantageous so that the views "from above" (anterior) may be implemented without auxiliary devices.

An irradiation field (e.g., positions of fins or plates of a collimator and/or a multilevel collimator (MLC) and irradiation direction (gantry position)) may be determined and/or restricted by record and verify (R&V) data of an irradiation plan. The use of real-time control data and/or measuring data (e.g., real time data) of redundant sensors of the corresponding components enables a visual verification by clinical personnel that is independent of the R&V data (e.g., an R&V system). The conventional optical collimation of the radiation field with the aid of a light source in the real isocenter may no longer be used. A useful installation height in the emitter head, which includes the radiation source, is herewith obtained.

An embodiment of a verification method of an irradiation field enables the moveable laser system to be used for virtual computed tomography (CT) simulation in order to define the patient and field marker if an imaging system (e.g., CT system) is integrated in the radiation therapy device.

BRIEF DESCRIPTION OF THE DRAWING

FIG. 1 shows an embodiment of a radiation therapy device.

DETAILED DESCRIPTION OF THE EMBODIMENTS

A patient P is adjusted by an additional laser system per projection PJ in front of an imaging system (e.g., of a radiotherapy device). A reference point (e.g., virtual isocenter VIZ) in front of the imaging system and the isocenter IZ of the imaging system are defined and are set and/or compensated accordingly in relation R by a patient couch PT.

The reference point is arranged "OFF isocentric." In other words, the reference point is optically shown outside of the isocenter IZ and/or at a distance from the isocenter IZ of the radiation therapy device. The patient may be moved with the patient couch PT into the isocenter.

The following acts are implemented for radiation therapy in order to verify an irradiation field BSF. By projecting at least one cross laser KL, the patient may be adjusted in the virtual isocenter VIZ. In other words, a positioning of the patient takes place using patient couch movements until the cross lasers KL correspond with at least one marker and/or field marker FM1, FM2 on the patient skin or immobilization aids. With the aid of the additional, optionally moveable laser system, the irradiation fields are projected onto the patient surface.

The irradiation field (e.g., positions of fins or plates of a multi level collimator MLC and irradiation direction (gantry position)) is determined by real time data for activating the fins and redundant sensor measurement of the corresponding components. The irradiation field is thus independent of R&V data of an irradiation plan. Machine-specific adjustment problems of mechanical or electronic origin in a linear accelerator LINAC may be visually identified by clinical personnel.

A compact emitter head that includes a radiation source SQ may be embodied along radiation axis A by omitting the mirror cited in the background.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radiation therapy device comprising:
   an irradiation field limiting apparatus comprising:
      a collimator operable to set an irradiation field; and
      a verification apparatus operable to visually verify the irradiation field, the verification apparatus comprising a light-emitting system operable to emit a light beam,
   wherein the verification apparatus is configured to optically indicate the irradiation field on a patient that is positioned at a distance from a beam path of a beam generateable by the radiation therapy device.

2. The radiation therapy device as claimed in claim 1, wherein the verification apparatus is arranged outside of the irradiation field limiting apparatus.

3. The radiation therapy device as claimed in claim 2, wherein the verification apparatus is arranged so as to be moveable.

4. The radiation therapy device as claimed in claim 2, wherein the verification apparatus comprises a light-emitting system.

5. The radiation therapy device as claimed in claim 2, wherein the verification apparatus is operable to indicate the irradiation field as a function of measurement data that characterize an adjustment of the collimator, as a function of control data for adjusting the collimator, or a combination thereof.

6. The radiation therapy device as claimed in claim 1, wherein the verification apparatus is arranged so as to be moveable.

7. The radiation therapy device as claimed in claim 6, wherein the verification apparatus comprises a light-emitting system.

8. The radiation therapy device as claimed in claim 6, wherein the verification apparatus is operable to indicate the irradiation field as a function of measurement data that characterize an adjustment of the collimator, as a function of control data for adjusting the collimator, or a combination thereof.

9. The radiation therapy device as claimed in claim 1, wherein the light-emitting system is operable to output a laser beam.

10. The radiation therapy device as claimed in claim 9, wherein the light-emitting system is operable to output a cross laser beam.

11. The radiation therapy device as claimed in claim 10, wherein the verification apparatus is operable to indicate the irradiation field as a function of measurement data that characterize an adjustment of the collimator, as a function of control data for adjusting the collimator, or a combination thereof.

12. The radiation therapy device as claimed in claim 9, wherein the light-emitting system is operable to simulate an imaging system that is integrateable in the radiation therapy device or connected to the radiation therapy device.

13. The radiation therapy device as claimed in claim 1, wherein the verification apparatus is operable to indicate the irradiation field as a function of measurement data that characterize an adjustment of the collimator, as a function of control data for adjusting the collimator, or a combination thereof.

14. The radiation therapy device as claimed in claim 1, wherein the light-emitting system is operable to simulate an imaging system that is integrateable in the radiation therapy device or connected to the radiation therapy device.

15. A method for verifying an irradiation field, the method comprising:
   positioning a patient outside of a beam path of a beam generateable by a radiation therapy device;
   projecting at least one light beam onto a target area lying outside of the isocenter of the radiation therapy device while the patient is positioned at a distance from the beam path;
   aligning the at least one light beam with at least one predetermined marker; and
   optically displaying the at least one light beam.

16. The method as claimed in claim 15, further comprising:
   determining the at least one marker on a skin surface of a patient; and
   aligning the at least one light beam with the at least one marker using patient couch movements.

17. The method as claimed in claim 15, wherein the at least one light beam represents a laser beam.

18. The method as claimed in claim 17, wherein the at least one light beam represents a cross laser beam.

19. The method as claimed in claim 15, wherein the positioning comprises positioning the patient at a distance of more than 20 cm from the isocenter.

* * * * *